U.S. Patent  Nov. 16, 1976  Sheet 1 of 2  3,992,114
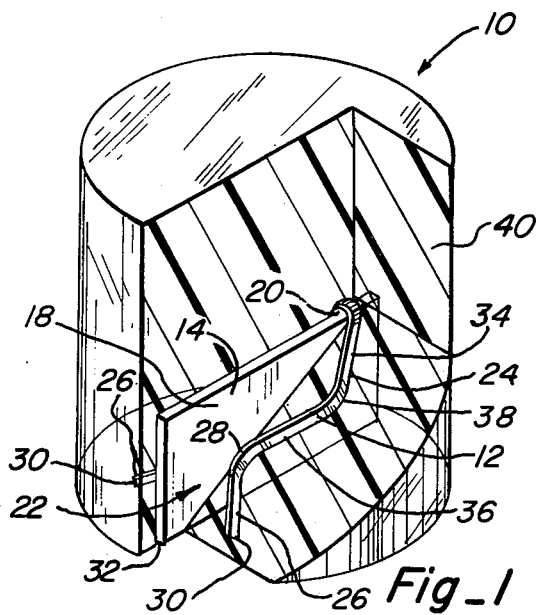
Fig_1
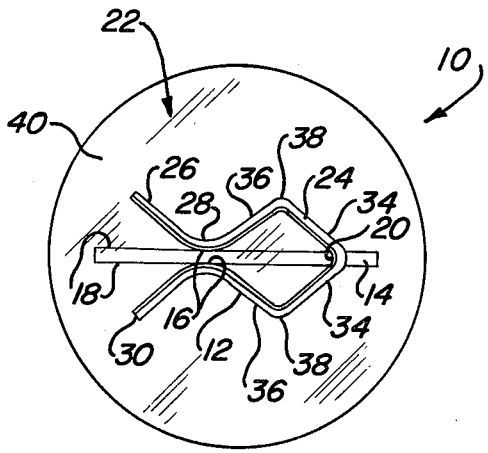
Fig_2
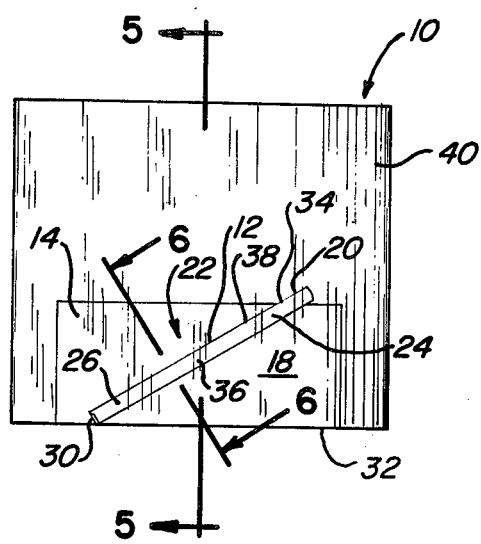
Fig_3
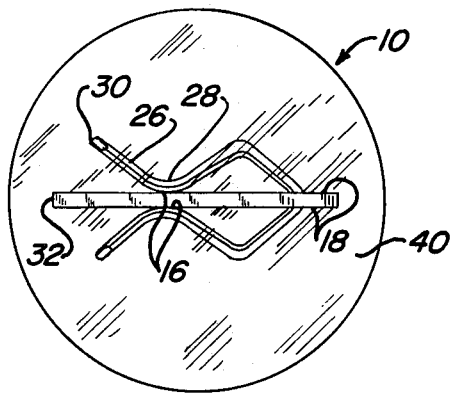
Fig_4
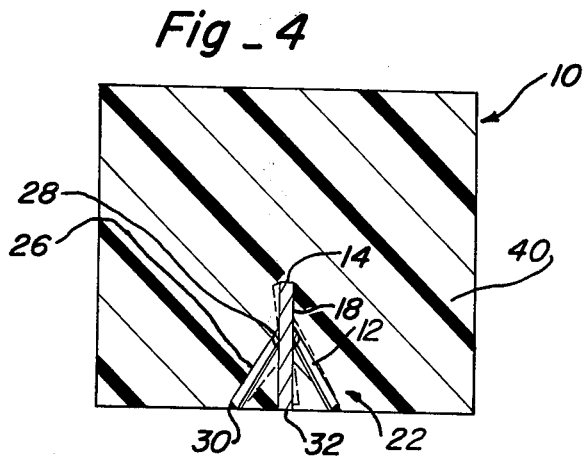
Fig_5
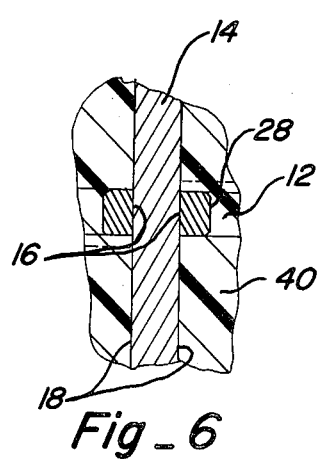
Fig_6

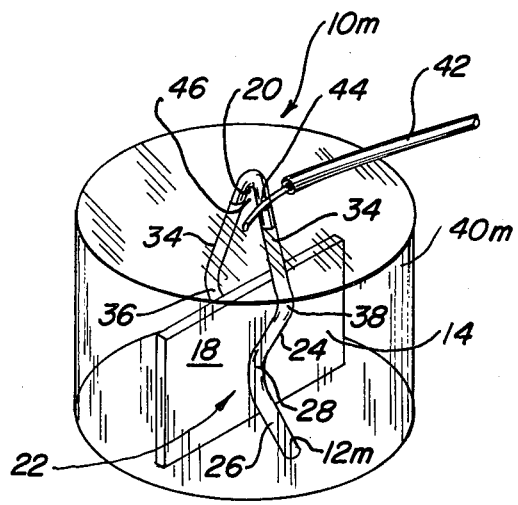
Fig_7
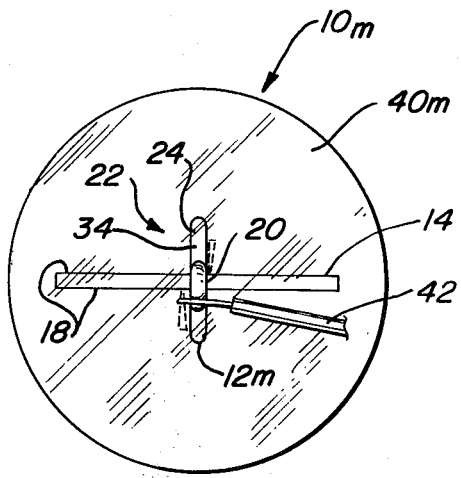
Fig_8
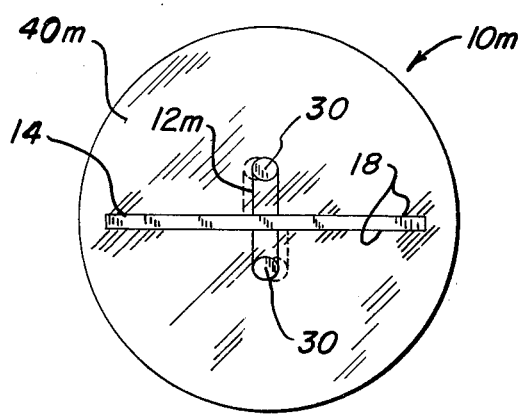
Fig_9
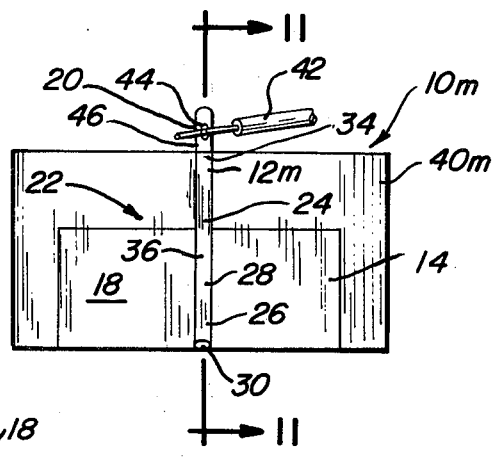
Fig_10
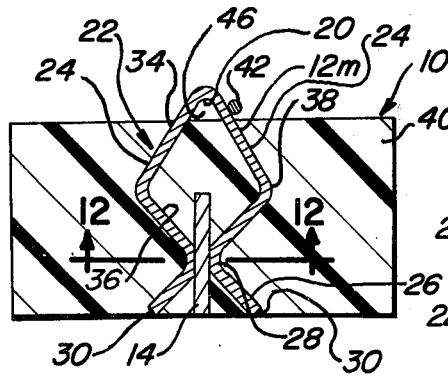
Fig_11
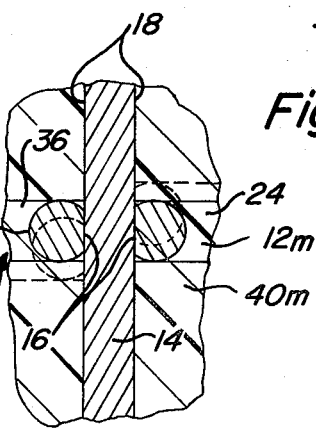
Fig_12

SPRING WIRE CLIP-TYPE SPECIMEN STAND

In the analysis of metallurgical specimens, the material to be analyzed is first cut into a small more or less rectangular plate which is usually about an inch long, somewhat less than an inch wide and anywhere from under a thousandth of an inch thick up to one thick enough to stand alone. Such a plate is then supported in upright position resting on one of its side edges while being permanently imbedded and cast into a block of suitable plastic material. The specimen along with its stand will usually end up encapsulated within a rigid cylinder of plastic in position such that the edge upon which it rested lies flush with one of its right truncated ends. Then, just prior to being subjected to micro or macro examination, the end of the block containing the edge of the specimen will be ground off flat to expose the latter and then polished. In some instances, the edge of the specimen thus exposed will be electrochemically etched by immersing the bottom surface of the assembly in an etching solution while passing an electrical current through the specimen itself.

Now, it is a stand for holding the specimen erect on one edge while it is being encapsulated that forms the subject matter of the present invention. This same clip may be employed to perform the additional function of an electrical conductor to conduct current from an outside power source into the encapsulated specimen when the latter is going to be electrochemically etched.

Spring clips for the primary purpose of holding the specimen upright on edge while being encapsulated have been known in the prior art for some time, the most widely used one consisting of a coil of spring metal ribbon a few thousandths of an inch thick and about a quarter of an inch wide. This single coil has about half of it unwound and rewound into a second coil alongside the first, the two of which receive the specimen therebetween in book-end like fashion. While thus supported in upright position gripped between the adjacent oppositely wound spring coils of the stand, the specimen and stand are encapsulated in the usual way.

Unfortunately, the spring coil-type specimen stand has a few shortcomings that render it less than satisfactory for its intended purpose. First of all, with the coils disposed at one end of the specimen, it becomes extremely difficult to polish it uniformly over its entire length, the latter being a condition which is highly desirable.

Another problem is that of having the convolutions of the coils tangent to the sides of the specimen along the edge thereof being examined. Here again, this is not considered good metallurgical practice.

The other major problem is one of air bubble entrapment between the closely-wound convolutions of the coils and, more importantly, between the intermost convolution and the face of the specimen it contacts. The presence of bubbles and the voids resulting therefrom are not conducive to a good examination and, therefore, are to be avoided.

It has now been found in accordance with the teaching of the instant invention that these and other shortcomings of the prior art coiled-ribbon specimen stands can be eliminated by the simple, yet unobvious expedient of straddling and gripping the specimen between the limbs of a uniquely-shaped hairpin-like spring wire clip, the terminal ends of which are spread apart cooperating with one another and the specimen itself to define a tripod-like stand. The two, or at most three, points at which the clip engages the specimen are all remote from the polished or etched edge being examined. Also, those portions of the clip immediately adjacent the contact points are all steeply inclined relative thereto so as to virtually eliminate the pockets where air bubbles are likely to form. Furthermore, the clip is ideally suited for use with specimens that will be electrochemically etched as it can be mounted thereon so as to provide an external appendage projecting beyond the mounting block to which an electrical lead can be attached for the transmission of current to the specimen.

Accordingly, it is the principal object of the present invention to provide a novel and improved spring clip-type wire stand for use in supporting metallurgical specimens and the like in an upright position on one edge.

A second objective is the provision of a device of the type aforementioned wherein the points of contact between the clip and specimen are nowhere near the edge of the latter being examined.

Another object of the invention herein disclosed and claimed is to provide a specimen clip which is devoid of structures which, either alone or in combination with the specimen, are susceptible of entrapping air.

Still another objective is the provision of a clip of the character described that is ideally suited for use as a conductor of those specimens which will be electrochemically etched.

An additional object is to provide a specimen clip that has no portion thereof contacting the edge to be examined or interfering with the polishing of the latter.

Further objects are to provide a spring wire clip-type holder for use as a specimen stand that is simple, inexpensive, lightweight, easy to install, versatile, dependable, rugged, foolproof and even somewhat decorative in appearance.

Other objects will be in part apparent and in part pointed out specifically hereinafter in connection with the description of the drawings that follows, and in which:

FIG. 1 is a perspective view, the right half of the block encapsulating the specimen having been truncated in the plane of the clip to more clearly reveal the latter;

FIG. 2 is a top plan view;

FIG. 3 is a right side elevation;

FIG. 4 is a bottom plan view;

FIG. 5 is a vertical section taken along line 5—5 of FIG. 3;

FIG. 6 is a fragmentary sectional detail to an enlarged scale taken along line 6—6 of FIG. 3;

FIG. 7 is a perspective view like FIG. 1 except that it shows a slightly modified version of the clip mounted on the specimen in an upright position with the crotch thereof projecting outside the block to receive an electrical lead;

FIG. 8 is a top plan view of the modification of FIG. 7;

FIG. 9 is a bottom plan view;

FIG. 10 is a right side elevation;

FIG. 11 is a vertical section taken along line 11—11 of FIG. 10; and,

FIG. 12 is a fragmentary section to an enlarged scale taken along line 12—12 of FIG. 11.

sufficient to cover the exposed lower edge of the specimen as well as the toes 30 of the clip, an electrical circuit is, of course, completed. Such a procedure is simple and far less time consuming than drilling into the block and into the specimen preparatory to inserting a screw or other contact into the latter. The protruding crotch 20 also cooperates with the adjacent surface of the block to define an eyelet 46 which constitutes a convenient appendage for emersing it in the etch solution.

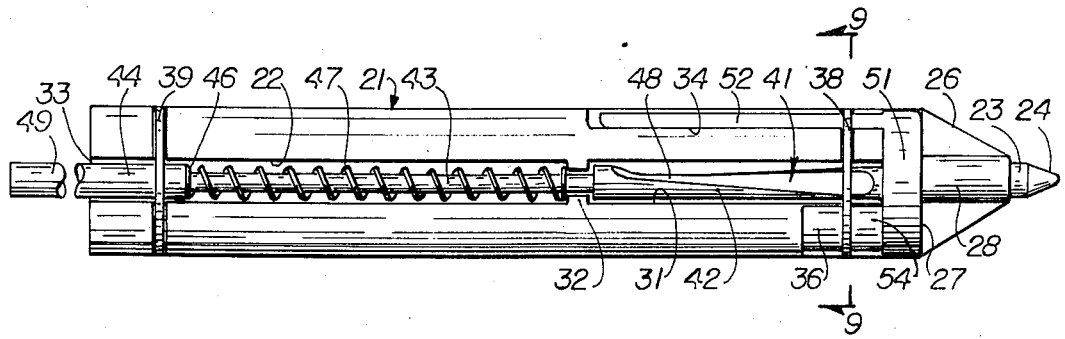

What is claimed is:

1. A clip for standing metallurgical specimens on edge while being encapsulated which comprises: a length of spring wire bent at a point midway between its ends to produce a V-shaped crotch joining a pair of substantially identical but oppositely curved generally S-shaped limbs in side-by-side relation, said limbs including oppositely arched portions diverging from the crotch and converging at points remote therefrom to define a pair of heels biased into engagement with one another and adapted to squeeze a plate-like specimen therebetween, and said limbs including foot-like portions diverging from the heels that terminate in spaced toes positionable in coplanar relation with a point on the bottom edge of the specimen misaligned therewith to define a tripod stand therefor.

2. The specimen clip as set forth in claim 1 in which: the limbs are mirror-images of one another.

3. The specimen clip as set forth in claim 1 in which: the crotch is positioned and adapted upon tiltable movement of the clip with its limbs astraddle the specimen to seat atop thereof and cooperate therewith and with the toes to maintain said specimen in an upright position on the supporting surface upon which it rests.

4. The specimen clip as set forth in claim 1 in which: the limbs are substantially coplanar.

5. The specimen clip as set forth in claim 1 in which: the knees include exposed contacting surfaces shaped to engage opposite parallel faces of the specimen and maintain same in upright position therebetween without the crotch being seated atop thereof and the limbs askew.

6. The specimen clip as set forth in claim 1 in which: the arched portions have a dogleg configuration.

7. The specimen clip as set forth in claim 1 in which: the distance separating the plane of the toes from the crotch is greater than the height of the specimen to be supported therebetween for positioning said crotch in spaced relation above the latter.

8. The specimen clip as set forth in claim 3 in which: the limbs are substantially coplanar so as to cooperate with one another and with the crotch when seated atop the specimen to maintan the latter in perpendicular position relative to the supporting surface upon which it rests.

9. The specimen clip as set forth in claim 5 in which: the limbs are coplanar and the opposed contacting surfaces make essentially spaced parallel line contact with the specimen.

10. The specimen clip as set forth in claim 5 in which: the opposed contacting surfaces are parallel.

11. In combination: a plate-like specimen; a length of spring wire bent at a point intermediate its ends to define a pair of generally S-shaped limbs positioned astraddle the specimen and biased into electrically conductive engagement therewith said limbs terminating in divergent feet cooperating with the specimen therebetween to stand the latter on edge; and means of encapsulating said specimen and said clip so as to leave the bend at the juncture between the limbs exposed for the connection of a conductor of electrical energy.

* * * * *

United States Patent [19]
Culver

[11] 3,992,115
[45] Nov. 16, 1976

[54] SELF-CONTAINED CLOSURE FOR WRITING INSTRUMENTS AND THE LIKE

[76] Inventor: Craig F. Culver, 201 Ware Road, Woodside, Calif. 94062

[22] Filed: Nov. 10, 1975

[21] Appl. No.: 630,265

[52] U.S. Cl. .................................. 401/106; 401/107
[51] Int. Cl.² ...................... B43K 9/00; B43K 24/00
[58] Field of Search ............................ 401/104–107

[56] References Cited
UNITED STATES PATENTS

| | | | |
|---|---|---|---|
| 2,416,112 | 2/1947 | Moore | 401/106 |
| 2,559,555 | 7/1951 | Zepelovich | 401/104 |

FOREIGN PATENTS OR APPLICATIONS

| | | | |
|---|---|---|---|
| 286,888 | 11/1949 | Switzerland | 401/104 |
| 2,209,265 | 8/1973 | Germany | 401/106 |

Primary Examiner—Lawrence Charles
Attorney, Agent, or Firm—Julian Caplan

[57] ABSTRACT

A pen, scribe or similar instrument fits into and projects out one end of a central axial aperture in a barrel. The barrel has a longitudinal groove in its surface and angularly displaced depressions in its outer surface at the end from which the pen projects. A cap assembly has an elongated shaft axially movable and oscillatable in the longitudinal groove and held in place by an upper and lower spring around the barrel. A helical spring biases the shaft toward retracted position with an end of the shaft projecting out the end of the barrel opposite the pen. The upper end of the shaft carries a fitting having a pocket clip and a pen cap. In retracted position, the clip and cap fit into their respective depressions. By depressing the shaft end against the force of the spring the clip and cap are raised and the spiral groove and upper spring cause them to pivot with the shaft until the cap is above the tip of the pen and the clip projecting outward of the barrel. The spring then partially projects the shaft end and the cap covers the pen tip. The closure is manually returned to original position. A modified construction is described.

10 Claims, 9 Drawing Figures